United States Patent
Roessl et al.

(10) Patent No.: US 9,664,797 B2
(45) Date of Patent: May 30, 2017

(54) DETECTOR UNIT WITH PULSE SHAPER

(71) Applicant: KONINKLIJKE PHILIPS N.V., Eindhoven (NL)

(72) Inventors: Ewald Roessl, Henstedt-Ulzburg (DE); Roger Steadman-Booker, Aachen (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 200 days.

(21) Appl. No.: 14/648,735

(22) PCT Filed: Dec. 12, 2013

(86) PCT No.: PCT/IB2013/060855
§ 371 (c)(1),
(2) Date: Jun. 1, 2015

(87) PCT Pub. No.: WO2014/091444
PCT Pub. Date: Jun. 19, 2014

(65) Prior Publication Data
US 2015/0309188 A1 Oct. 29, 2015

Related U.S. Application Data

(60) Provisional application No. 61/737,145, filed on Dec. 14, 2012.

(51) Int. Cl.
*H05G 1/64* (2006.01)
*G01T 1/17* (2006.01)
*G01N 23/04* (2006.01)

(52) U.S. Cl.
CPC ............... *G01T 1/17* (2013.01); *G01N 23/04* (2013.01); *G01T 1/171* (2013.01)

(58) Field of Classification Search
None
See application file for complete search history.

(56) References Cited

U.S. PATENT DOCUMENTS

| | | | |
|---|---|---|---|
| 6,759,658 B2* | 7/2004 | Overdick | G01N 23/046 250/336.1 |
| 7,388,534 B2* | 6/2008 | Astley | G01T 1/17 341/155 |
| 8,350,221 B2* | 1/2013 | Steadman Booker | G01T 1/17 250/336.1 |

(Continued)

FOREIGN PATENT DOCUMENTS

| | | |
|---|---|---|
| DE | 102007033671 A1 | 1/2008 |
| WO | 2009050619 A2 | 4/2009 |
| WO | 2009133481 A2 | 11/2009 |

*Primary Examiner* — Andrew Smyth

(57) ABSTRACT

The invention relates to a detector unit (100) for the detection of photons of incident radiation. The detector unit (100) comprises a signal processing circuit (40, 50, 60) for generating signals (V0) that are dependent on the energy of a currently detected photon (X) and at least one processing-parameter (Rf). Moreover, it comprises a flux estimator (70) for estimating the flux of photons and for adjusting the processing-parameter (Rf) based on said estimated flux. The flux estimator (70) receives its input (Vi), from which the flux of photons is estimated, from a processing stage that is independent of the output of the signal processing circuit. In a preferred embodiment, the signal processing circuit is or comprises a shaper (40).

9 Claims, 1 Drawing Sheet

(56) References Cited

U.S. PATENT DOCUMENTS

| | | | |
|---|---|---|---|
| 8,415,635 B2 * | 4/2013 | Marks | G01T 1/171 250/370.09 |
| 2007/0098139 A1 * | 5/2007 | Hoffman | A61B 6/4241 378/19 |
| 2008/0018505 A1 * | 1/2008 | Astley | G01T 1/17 341/51 |
| 2009/0129537 A1 * | 5/2009 | Rao | G06G 7/18 378/4 |
| 2010/0172467 A1 * | 7/2010 | Steadman Booker | G01T 1/17 378/19 |
| 2010/0193700 A1 * | 8/2010 | Herrmann | G01T 1/171 250/395 |
| 2010/0207027 A1 * | 8/2010 | Marks | G01T 1/171 250/336.1 |
| 2011/0036989 A1 * | 2/2011 | Marks | G01T 1/17 250/370.08 |
| 2011/0211670 A1 * | 9/2011 | Dugas | G01N 23/223 378/45 |
| 2012/0201339 A1 * | 8/2012 | Nakamura | G21C 17/108 376/254 |
| 2012/0236986 A1 * | 9/2012 | Schroter | G01T 1/247 378/19 |
| 2013/0287172 A1 * | 10/2013 | Hermann | H01L 27/14643 378/62 |

* cited by examiner

DETECTOR UNIT WITH PULSE SHAPER

CROSS REFERENCE TO RELATED APPLICATIONS

This application is a national filing of PCT application Serial No. PCT/IB2013/060855, filed Dec. 12, 2013, published as WO 2014/091444 A1 on Jun. 19, 2014, which claims the benefit of U.S. provisional application Ser. No. 61/737,145 filed Dec. 14, 2012, which is incorporated herein by reference.

FIELD OF THE INVENTION

The invention relates to a detector unit for the detection of photons of incident radiation, particularly X-radiation, said detector unit comprising a signal processing circuit for generating signals dependent on photon energy. Moreover, it relates to a radiation detector and to an imaging apparatus for generating images of an object, and to a method for the processing of electrical signals indicative of detected photons.

BACKGROUND OF THE INVENTION

The US 2007/0098139 A1 discloses a method and a system for an energy-resolved counting of X-ray photons. The system comprises a charge amplifier in which charge signals corresponding to detected photons are amplified, a signal shaper in which pulses corresponding to the charge signals are generated, an energy level discriminator in which said pulses are discriminated with respect to photon energy, and a counter for counting the number of detected and discriminated pulses. Moreover, the system comprises a controller that receives the output of the counter and that adjusts the shaping time of the signal shaper based on this photon count feedback.

SUMMARY OF THE INVENTION

It would be advantageous to have means that allow for an improved detection of radiation, particularly of X-radiation over a large dynamic range of flux levels.

This object is addressed by a detector unit, a radiation detector, an imaging apparatus, and a method. Preferred embodiments are disclosed in the dependent claims.

According to a first aspect, the above mentioned concerns are addressed by a detector unit for the detection of photons of incident radiation, particularly of X-ray or gamma photons. The detector unit comprises the following components:

A signal processing circuit for generating signals that are dependent on the energy of the currently detected photon (which contributes to said signal) and at least one parameter that is inherent to the signal processing circuit and that will be called "processing-parameter" in the following.

A flux estimator for estimating the flux of photons and for adjusting the aforementioned processing-parameter of the signal processing circuit based on said estimated flux, wherein the flux estimator receives its input signals (from which the flux of photons is estimated) from a processing stage that is independent of the output of the signal processing circuit.

The detector unit will typically comprise further components which are not explicitly mentioned above because their realization is not essential in the context of the present invention, for example components for converting incident photons into electrical signals, or components for evaluating the generated signals.

As usual, the "flux of photons" is defined as the number of incident photons per unit of time (measured e.g. in counts per second (cps)).

The "processing stage that is independent of the output of the signal processing circuit" may be a processing stage within the signal processing circuit, though it will preferably be a processing stage lying in front of the signal processing circuit with respect to signal flow. Moreover, the independence is usually unidirectional only, i.e. said processing stage is (causally) independent from the output of the signal processing circuit but not vice versa.

The described detector unit has the advantage that it allows for an accurate detection of incident photons over a large range of flux levels because the present flux of photons is estimated and used to adjust the processing of the electrical signals representing detected photons. Thus the processing can always be kept in an optimal range, allowing for example for an accurate detection of photon energy at both low flux levels and high flux levels. The accuracy of this adjustment is particularly high because the estimation of the present photon flux is independent of the output of the signal processing circuit. In the US 2007/0098139 A1, flux is determined from the output of the counter, and adaptation due a change of flux can only be made with respect to the future, based on previous events. In contrast to this, the described detector unit allows for an adjustment of the processing-parameter that is used for the processing of the currently detected photon wherein the contribution of said very photon to flux can already be taken into account. Thus it is possible to react to changes of flux within projections. In the extreme case, a detected photon may affect, via its contribution to the estimated flux, its own processing by the signal processing circuit.

According to one particular embodiment of the detector unit, the input of the flux estimator (receiving the signals from which the present flux is estimated) is connected to an integrating channel that generates a signal indicative of the integrated detected photon energy. The (temporal) integration of detected photon energy will usually be done in a temporally weighted manner, wherein more recent events are given a higher weight than older events. Typically, the integration period is restricted to some given time window. The signal of the integrating channel provides some kind of moving average of radiation intensity (i.e. of deposited energy per unit of time), from which the photon flux can be derived if the average energy carried by the photons is known.

The aforementioned embodiment is particularly favorable in connection with detector units in which an integrating channel is already available parallel to the channel comprising the signal processing circuit and the flux estimator. The integrating channel may particularly derive its signals from the same and/or from different photon-detection events than those that are processed by the signal processing circuit (i.e. the integrating channel may process the signals of the same pixel(s) as the signal processing circuit and/or of other pixel(s) than the signal processing circuit).

According to another embodiment, the input of the flux estimator (receiving the signals from which the flux is estimated) and the input of the signal processing circuit may be connected to a common signal source. This means that the flux estimator and the signal processing circuit are provided directly or indirectly (i.e. via intermediate components) with the same input signals. Accordingly, signals generated by incident photons are processed in parallel by the flux estimator and the signal processing circuit.

The flux estimator may comprise an integrator for the (temporal) integration of an input, particularly of electrical signals indicative of detected photons. The integration may preferably correspond to a weighted temporal summation of input signals representing the detected photons.

The detector unit may optionally comprise a conversion unit in which incident photons are converted into charge signals. This may particularly be a direct conversion unit comprising an appropriate converter material (e.g. CdTe, CZT) that directly converts incident photons into electron-hole pairs in the conduction resp. valence band of the material. Alternatively, the conversion unit may comprise a scintillator in which incident (X-ray or gamma) photons are converted into photons of lower energy that can be detected e.g. by photodiodes.

The aforementioned detector unit may optionally further comprise a charge sensitive amplifier for receiving and amplifying the output of its conversion unit. The output of the conversion unit and/or of the charge sensitive amplifier are examples of a common signal source to which, in the above mentioned embodiment of the detector unit, the flux estimator and the signal processing circuit may both be connected.

In a preferred embodiment of the detector unit, the signal processing circuit may comprise a shaper for generating an electrical pulse with a shape determined by the energy of a currently detected photon (which triggers said pulse) and the processing-parameter (i.e. at least one of the processing-parameters, if there are several). Said processing-parameter of the shaper will in the following also be called "shape-parameter". By adapting the shape-parameter, the flux estimator can always keep the pulse shape in an optimal range for processing, allowing for example for an accurate detection of photon energy at both low flux levels (using longer pulses) and high flux levels (using shorter pulses). In many embodiments, the signal processing circuit may comprise nothing but the shaper (i.e. the term "signal processing circuit" can be replaced with "shaper" for these embodiments).

The shaper may be realized in many different ways. In a preferred embodiment, it comprises an amplifier with a feedback path comprising a resistor and/or a capacitor. A shaper with such elements is for example known from the WO 2009/133481 A2 which is incorporated into the present application by reference.

In a further development of the aforementioned embodiment, the flux estimator may be able to adapt said resistor and/or said capacitor in the feedback path of the amplifier. If the resistor is for example realized by a transistor, its gate may be controlled by the feedback estimator. This provides a simple and fast means via which the flux estimator can control an essential processing-parameter of the shaper.

In another embodiment, the signal processing circuit may comprise an (additional) amplification stage with a variable gain amplifier for amplifying the output of a shaper (e.g. a shaper of the above mentioned kind). The gain of this amplifier may then be a processing-parameter that can be adjusted by the flux estimator. Thus it is for example possible to restore the shaper's output level if it decreases due to increasing flux levels.

The detector unit may further comprise a set of discriminators, wherein each discriminator can discriminate (classify) signals according to the energy of the photon which is represented by said signal. The discriminators may particularly be coupled to the output of the above mentioned shaper, wherein each discriminator can discriminate each pulse generated by the shaper. This allows for an energy-resolved detection of the incident radiation.

In a further development of the aforementioned embodiment, the flux estimator is adapted to further adjust at least one operating parameter of at least one of the discriminators (said discriminator hence being a part of the "signal processing circuit" and said operating parameter being an example of a "processing-parameter"). The flux estimator may for example be adapted to adjust the thresholds of the discriminators, in particular in such a way that the thresholds are lowered with increasing flux. This can counteract a decrease of pulse-heights with increasing flux levels.

The detector unit may further optionally comprise at least one counter for counting pulses generated by the shaper, thus allowing for the implementation of a photon counting detection scheme. This embodiment may particularly be combined with the aforementioned one, yielding an energy-resolved photon counting detection. The counter may optionally be considered as a part of the signal processing circuit or not.

In a second aspect, the concerns of the state of the art are addressed by a radiation detector comprising an array of detector units of the kind described above. In this context, the term "array" shall denote an arbitrary one-, two- or three-dimensional arrangement of units. Most preferably, the radiation detector comprises a two-dimensional array of regularly arranged detector units, each unit corresponding to a "pixel" of a projection image that can be generated with the radiation detector.

In the aforementioned radiation detector, the detector units may each have their own signal processing circuit and associated flux estimator. Additionally or alternatively, there may be at least two detector units that share a signal processing circuit or, more preferably, a flux estimator.

In a third aspect, the concerns of the state of the art are addressed by an imaging apparatus for generating images of an object (e.g. a body part of a patient, a piece of luggage etc.). The imaging apparatus comprises the following components:
  A radiation source for emitting radiation towards the object.
  A detector unit of the kind described above for detecting said radiation (typically after its passage through the object).

As explained above, the detector unit will comprise a signal processing circuit for generating a signal determined by the energy of the currently detected photon and at least one processing-parameter, and a flux estimator for estimating the flux of photons and for adjusting the processing-parameter based on said estimated flux, wherein the flux estimator receives its input from a processing stage that is independent of the output of the signal processing circuit.

The radiation source may particularly be an X-ray source allowing for the generation of X-ray projections of the object. Moreover, the imaging apparatus may particularly be designed as a Computed Tomography (CT) apparatus or scanner in which projection images of the object are generated from different viewing angles, allowing for a reconstruction of sectional or volumetric images of the object. Most preferably, the imaging apparatus may be a photon counting spectral (i.e. energy-resolved) CT scanner.

In a fourth aspect, the problems of the state of the art are addressed by a method for the processing of electrical signals indicative of detected photons, said method comprising the following steps:

a) Generating signals that are dependent on the energy of a currently detected photon and at least one processing-parameter.

b) Estimating the flux of photons based on signals that are independent of the aforementioned generated signals.

c) Adjusting the processing-parameter based on said estimated flux.

Steps a) and b) of the method are usually executed in parallel. Most preferably, steps b) and c) are executed (for a given detected photon) before step a).

The method, the imaging apparatus, the radiation detector, and the detector unit are different realizations of the same inventive concept, i.e. the adjustment of a processing-parameter of a signal processing circuit based on an estimation of photon flux. Explanations and definitions provided for one of these realizations are therefore valid for the other realizations, too.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

Figure 1:
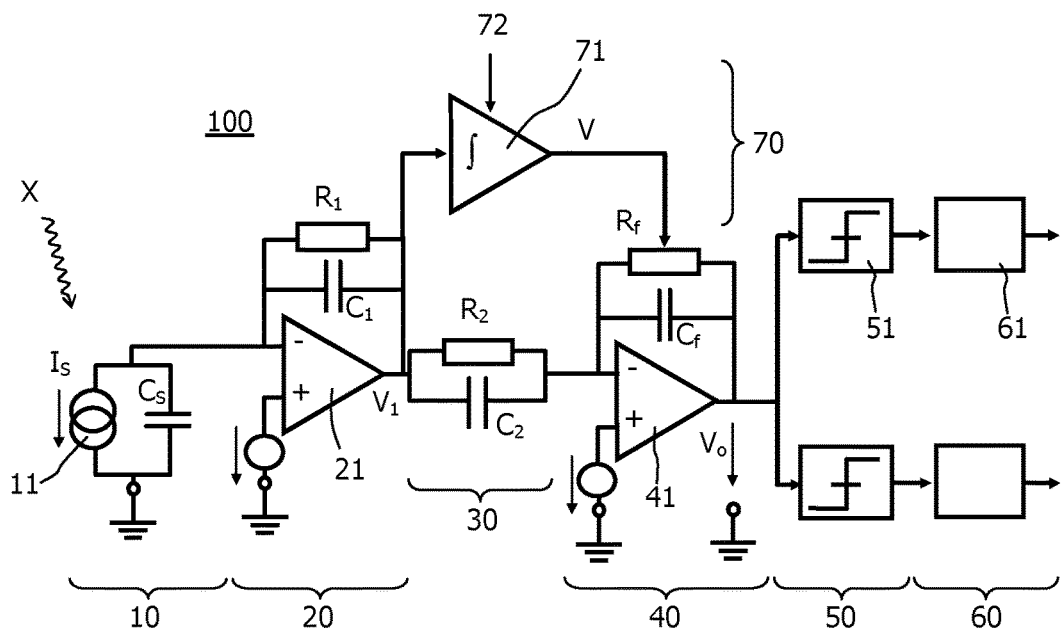
FIG. 1 shows a circuit diagram of a detector unit according to an embodiment of the present invention.

High rates and the related degradation of spectral performance are among the main obstacles to energy-discriminating, photon-counting spectral CT. Current read-out electronics of room-temperature semi-conductor detectors like CdTe or CZT have to find a compromise between rate performance and energy discrimination. At high rates, pulses typically tend to overlap and the corresponding complicated changes in the shaper output render a description of the processes and in particular the accurate prediction of the measured rate complicated to say the least. More importantly, of course, pile-up heavily jeopardizes the possibility to measure the energies of the impinging photons. It would therefore be desirable to improve energy performance in the low flux regime and rate-performance in the high flux regime at the same time.

In the design of every photon-counting electronic an important choice has to be made regarding the balance between rate performance and energy-discrimination performance. The bandwidth of a shaping circuit can be controlled typically by a feedback resistor and capacitor that control eventually both the rate performance and the energy performance. A certain choice for the values of those resistors and capacitors will lead to a certain rise time of the shaper output to an input from the semiconductor sensor. The faster the pulse rises (the faster the pulse is shaped) the faster the shaper output will be back at the baseline and ready for the next pulse. Hence, a fast shaper obviously enables handling higher rates. However, faster shaping comes also at a drawback: as the output of the charge sensitive amplifier has a relatively slowly decreasing tail, a fast shaper will tend to produce pulses with pulse heights less and less indicative of the true charge deposited in the sensor (and hence less and less indicative of the deposited energy) as the shaping time becomes shorter and shorter. This "ballistic deficit" leads typically to an underestimation of the deposited energy. The effect increases with energy so that the overall effect will be manifest in a non-linear relationship between the incident energy and the measured pulse-height of the photo-peak. As long as the detector behavior remains reproducible, this effect could to some degree be accounted for by calibration of the energy scale.

The above mentioned effects of a particular choice of shaping time are two prominent ones but there are others like noise performance and the level of saturation performance. However, they best illustrate the necessity for a compromise and the need to tune the detector parameters to the particular application.

In essence, for spectral CT applications, the shaping time of a detector is presently determined by the desired performance at high rates. For example, in the Philips proprietary ChromAIX ASIC, peaking times of about 10 ns were put into the design to accommodate input rates of about 36 Mcps and channel corresponding to an output count rate of about 13 Mcps and channel. Hence, the shaping time was determined by the rate performance. In a typical CT scan at least 95% of all channels relevant for image reconstruction are subject to much lower rates than the rate determining the ChromAIX design due to combined attenuation of the bowtie filter and more importantly from the patient. Hence, for the application CT, the majority of channels shape their pulses faster than necessary with the described consequence of too high ballistic deficit and unnecessary loss in spectral performance.

On the other hand, for the very few channels subject to very high rates, the ballistic deficit is not the major concern. In this regime, the rate performance is at its limit and energy discrimination is most heavily degraded by pileup, not ballistic deficit. Therefore, in this regime, peaking times even faster than the designed 10 ns would benefit the rate performance and likely improve energy performance as well due to reduced pileup and despite higher ballistic deficit.

Motivated by the above two extremes, it is proposed to dynamically adapt a processing-parameter, e.g. the shaping time, to the local, current flux level, individually for each channel.

FIG. 1 shows a circuit diagram of a detector unit 100 according to an embodiment of the above principles. The detector unit 100 is a single unit or "pixel" of a larger radiation detector that usually comprises several thousands of such detector units 100 arranged in a two-dimensional array for generating projection images of an object (not shown). More details about such a radiation detector and its integration in a CT scanner may be found in the WO 2009/133481 A2.

The detector unit 100 comprises a (direct) conversion unit 10 in which incident X-ray photons X are converted into electrical charge signals. The conversion unit 10 is only schematically represented by its equivalent circuit comprising a current source 11 parallel to a capacitor Cs.

The charge signal of the conversion unit 10 is provided to the negative input of a charge sensitive amplifier (CSA) 21 of a preprocessing unit 20. The positive input of said amplifier 21 is connected to mass, and the output voltage $V_1$ of the amplifier 21 is fed back to the negative input in parallel via a resistor $R_1$ and a capacitor $C_1$.

The output of the charge sensitive amplifier 21 is further provided to a filter 30 comprising a parallel arrangement of a further resistor $R_2$ and capacitor $C_2$ serving as a pole-zero cancellation (wherein preferably $R_2 \cdot C_2 = R_1 \cdot C_1$).

The output of the aforementioned filter 30 is connected to the (negative) input of a further amplifier 41 belonging to a shaper 40. The positive input of this amplifier 41 is connected to mass, and its output voltage $V_O$ is fed back to the negative input via a parallel arrangement of a resistor $R_f$ and a capacitor $C_f$.

The shaper 40 generates at its output pulses with shapes (especially heights) that correspond to the energy deposited by the photon X detected in the conversion unit 10. These pulses are provided to the inputs of a set 50 of discriminators 51 having different thresholds, such that the pulses (and thus the photon energies) are assigned to different levels or classes.

In a final processing stage, a set 60 of counters 61 is provided, each counter 61 being connected to the output of one discriminator 51 for counting the pulses passing said associated discriminator.

The described detector unit 100 thus provides for an energy-resolved photon counting detection of incident radiation.

In order to implement the proposed dynamic adaptation of shaping parameters to the current flux level, a flux estimator 70 is further added to the circuit of Figure 1. In the shown embodiment, the flux estimator 70 comprises an integrator 71 which receives as its input the output Vi of the charge sensitive amplifier 21. The output of the charge-sensitive amplifier (CSA) 21 can be considered a reliable measure of the average flux incident on the current detector channel in a given time period. Its bandwidth is an important design choice and determines how fast the shaper adapts to changes in flux. More particularly, the average voltage at the output of the CSA is usually a very good indication of the rate. So, that is what the integrator 71 should ultimately yield as output.

The output of the integrator 71, which gives an indication of the count-rate, acts on the resistor $R_f$ in the feedback path of the shaper's amplifier 41, thus controlling the value of its resistance. If the resistor $R_f$ is for example realized by a transistor, the output of the integrator 71 may control the gate of the transistor, making the resistance $R_f$ a function of the output voltage V according to a relation $R_f=f(V)$.

Additionally or alternatively, one could also modify the capacitance $C_f$ to adapt the peaking time/height, not only the ballistic deficit (which is modified with $R_f$).

At low flux levels the equivalent feedback resistor $R_f$ is adjusted to a large value to minimize the ballistic deficit of the shaper 40, improving the energy resolution. As the flux increases the feedback resistor $R_f$ can be consequently reduced to allow faster counting rates.

The shaper 40 hence constitutes a signal processing circuit for generating signals (the pulses $V_O$) that are dependent on the energy of a currently detected photon X and at least one adaptable "processing-parameter" or "shape-parameter" (the resistance $R_f$ and/or the capacitance $C_f$).

The described implementation has significant benefits compared to prior art, e.g. the US 2007/0098139 A1. In the latter, count rate is derived from the already acquired data. In other words, this is rather a slow feedback mechanism and may cause the shaper time constant to react too slowly to significant changes in flux. In fact, in an unlucky situation, one may even see that the shaper adaptation is fooled by sensing the number of counts in a situation where pile-up is so severe that the registered counts already dropped to a low value (according to a dead-time/paralyzable model). In the implementation suggested here, on the contrary, adaptations can be made within projections.

The integrator 71 of the flux estimator 70 requires a reset mechanism (indicated by a reset input 72) to allow reassessing the equivalent count-rate at given intervals. The choice of integrating interval and bandwidth of the integrator can be set to control the sensitivity of the shaping times to changing counting-rate.

Figure 2:
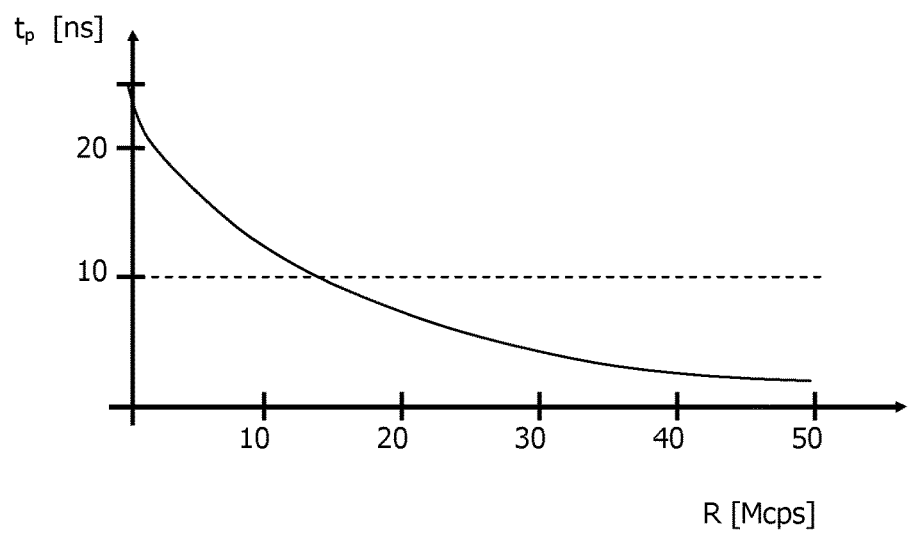
FIG. 2 shows the dependence of the peaking time on the flux for a shaper circuit.

A possible design chart for the dependence of the peaking time (i.e. the time at which, after start of a pulse, the peak of the pulse is reached) of the dynamic shaper 40 as a function of the incoming flux is shown in FIG. 2. The ChromAIX shaper is represented by the straight line corresponding to constant 10 ns shaping time independent of flux.

In the example shown, peaking times at very low flux will be around 25 ns guaranteeing a very small ballistic deficit in this regime. For intermediate rates of about 15 Mcps the shaper will be about as fast as the current ChromAIX shaper. For the high-rate situation, e.g. around 30 Mcps, the shaper would output pulses peaking after about 5 ns, significantly reducing pile-up and, hence, significantly linearizing OCR-vs.-ICR count-rate curves at the cost of an increased ballistic deficit. The reduction of pile-up and the corresponding improvement of energy-performance, however, will outweigh the increase of ballistic deficit. Moreover, the range at which the output count-rate increases linearly with flux is extended, shifting the maximum rate to higher values.

Additionally, the ever increasing ballistic deficit at faster and faster shaping at increasing flux can be partially counteracted by a multiplicative down-scaling of the comparator thresholds with flux. This would provide a hardware countermeasure to the decreasing pulse-height for faster shaping.

Additionally or alternatively, the shaper might include a variable gain amplifier (not shown; to be inserted between the amplifier 41 and the discriminators 51). Adaptation of the gain of this amplification stage could then be used to counteract changes of the pulse-height.

In another embodiment the flux measurement required to modify the shaping time can also come in connection with the integrating channel of a counting-integrating detector (as know e.g. from the U.S. Pat. No. 6,759,658, which is incorporated into the present text by reference). In this latter case, the integrator is right at the input and the input current has to be replicated to both integrator and counting channel.

In summary, embodiments were disclosed with the concept to dynamically modify the peaking time of the shaping circuit of an energy-sensitive photon-counting detector aimed at improving both, rate performance in the high-flux regime and energy-performance in the low-flux regime due to reduced ballistic deficit and noise.

The described embodiments can for example be used in all applications relating to photon-counting detectors where the trade-off between energy-performance and rate performance is an important design consideration, such as in energy-sensitive, photon-counting detectors for spectral CT.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A detector unit for the detection of photons of incident radiation, comprising:
   a conversion unit in which incident photons are converted into charge signals, wherein said charge signals are amplified by a charge sensitive amplifier,
   a signal processing circuit for generating signals that are dependent on the energy of a currently detected photon and at least one processing-parameter;
   a flux estimator for estimating the flux of photons and for adjusting the processing-parameter based on said estimated flux, wherein the flux estimator receives its input signals from a processing stage that is independent of the output of the signal processing circuit,
   wherein the signal processing circuit comprises a shaper for generating an electrical pulse with a shape determined by the energy of a currently detected photon and the processing-parameter, said shaper comprising an amplifier with a feedback path including a resistor and/or a capacitor,
   and wherein the flux estimator comprises an integrator which receives as its input the output of the charge sensitive amplifier and wherein the output of the integrator adjusts the resistor and/or the capacitor of the shaper.

2. The detector unit according to claim 1, wherein the input of the flux estimator is connected to an integrating channel that generates a signal indicative of the integrated detected photon energies.

3. The detector unit according to claim 1, wherein the input of the flux estimator and the input of the signal processing circuit are connected to a common signal source.

4. The detector unit according to claim 1, wherein the signal processing circuit comprises a variable gain amplifier and the flux estimator can adjust said gain.

5. The detector unit according to claim 1, wherein said detector unit comprises a set of discriminators for discriminating signals according to photon energy.

6. The detector unit according to claim 5, wherein the processing-parameter comprises at least one operating parameter of at least one discriminator.

7. The detector unit according to claim 1, wherein said detector unit comprises at least one counter for counting pulses.

8. A radiation detector, comprising an array of detector units according to claim 1.

9. An imaging apparatus for generating images of an object, comprising:
   a radiation source for emitting radiation towards the object;
   at least one detector unit according to claim 1 for detecting said emitted radiation.

* * * * *